United States Patent [19]

Stedtfeld et al.

[11] Patent Number: 4,592,362

[45] Date of Patent: Jun. 3, 1986

[54] LEG-SUPPORT FOR MAKING RESTRAINED-OBJECT X-RAY PHOTOGRAPHS OF THE KNEE JOINT

[75] Inventors: Hans-Werner Stedtfeld, Münster; Michael Strobel, Lippstadt, both of Fed. Rep. of Germany

[73] Assignee: Hermann Ruf, Del.X

[21] Appl. No.: 506,353

[22] Filed: Jun. 21, 1983

[30] Foreign Application Priority Data

Mar. 8, 1983 [DE] Fed. Rep. of Germany ....... 3308063

[51] Int. Cl.$^4$ ............................................. A61F 13/00
[52] U.S. Cl. .................................... 128/653; 378/195
[58] Field of Search ............... 128/653, 133, 69, 80 R, 128/80 C; 269/328; 378/195, 208, 209, 180

[56] References Cited

U.S. PATENT DOCUMENTS

| | | | |
|---|---|---|---|
| 4,232,681 | 11/1980 | Tulaszewski | 128/653 |
| 4,291,229 | 9/1981 | Patt | 378/180 |
| 4,407,277 | 10/1983 | Ellison | 128/133 |

OTHER PUBLICATIONS

Klassification der chronischen Kapselbandinslabilitaten des Kniegelenkes—Tiel 1: Anatomic and Diagnostik, Franke, 1981.
Ein Messgerat zur objektiven Festellung der Instabilitat des Kniegelenkes, Gude, 1980.
The Lateral Pivot Shift: A Symptom and Sign of Anterior Cruciate Ligament Insufficiency, Galway, 1980.
Experimentelle Untersuchungen zur Erklarung des Lachman-Testes, Hafner, 1981.
Abgrenzung der operativen und konservativen Behandlung frischer Bandverietzungen am oberen Sprunggelenk, Hagen et al., 1981.
Stabilizing Mechanisms of the Loaded and Unloaded Knee Joint, Hsieh et al., 1976.
Radiologic Technique for Measuring Instability in the Knee Joint.
Die Problematic veralteter, kombinierter Komplexinstabilitaten des Kniegelenkes.
Anterior Subluxation of the Lateral Tibial Plateau.
The Role of Joint Load in Knee Stability.
Clinical Laxity Tests and Functional Stability of the Knee: Biomechanical Concepts.
Experimentelle Untersuchungen zur Diagnose des Kniebandapparates.
Die "Gehaltene Aufnahme".
Rotatory Instability of the Knee.
Zur rontgenologischen Diagnostik von Kapselbandschaden am Kniegelenk.
Clinical Diagnosis of Anterior Cruciate Ligament Instability in the Athlete.

*Primary Examiner*—Edward M. Coven
*Attorney, Agent, or Firm*—Andrus, Sceales, Starke & Sawall

[57] ABSTRACT

What is described is a leg-supporting means for making restrained X-ray photographs of the knee joint. In order to obviate the disadvantages of the apparatus which are on the market for making X-ray photographs of the knee joint, more especially the unstable position of the proband leg and shift instabilities with small degrees of flexion, provision is made for a thigh section or member with two clamping members movable concentrically relatively to one another to be connected to a ring enclosing the X-ray zone for the knee joint, and for the ring with the thigh member to be rotatable relatively to a lower leg member about its center and by up to 90° towards both sides.

24 Claims, 9 Drawing Figures

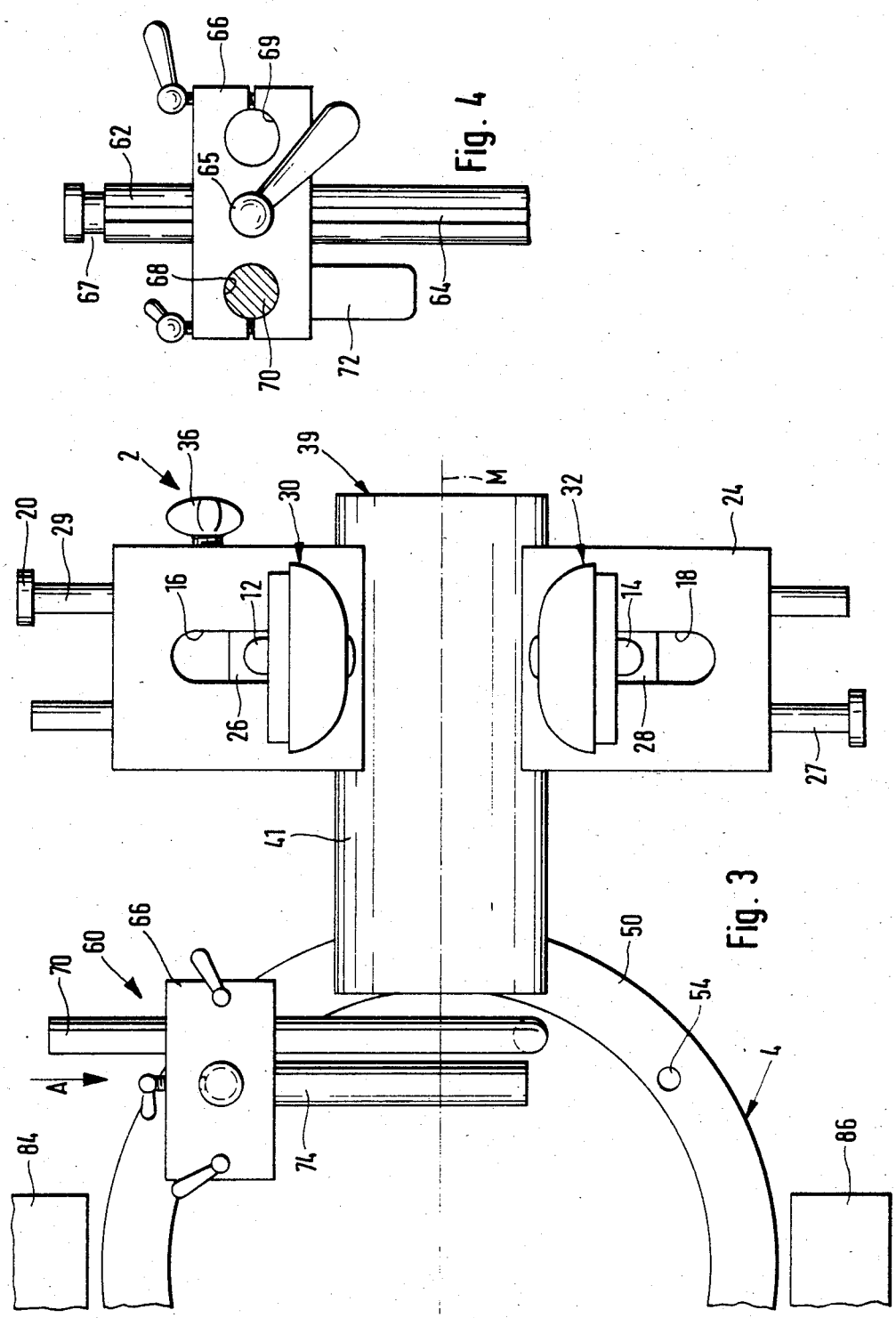

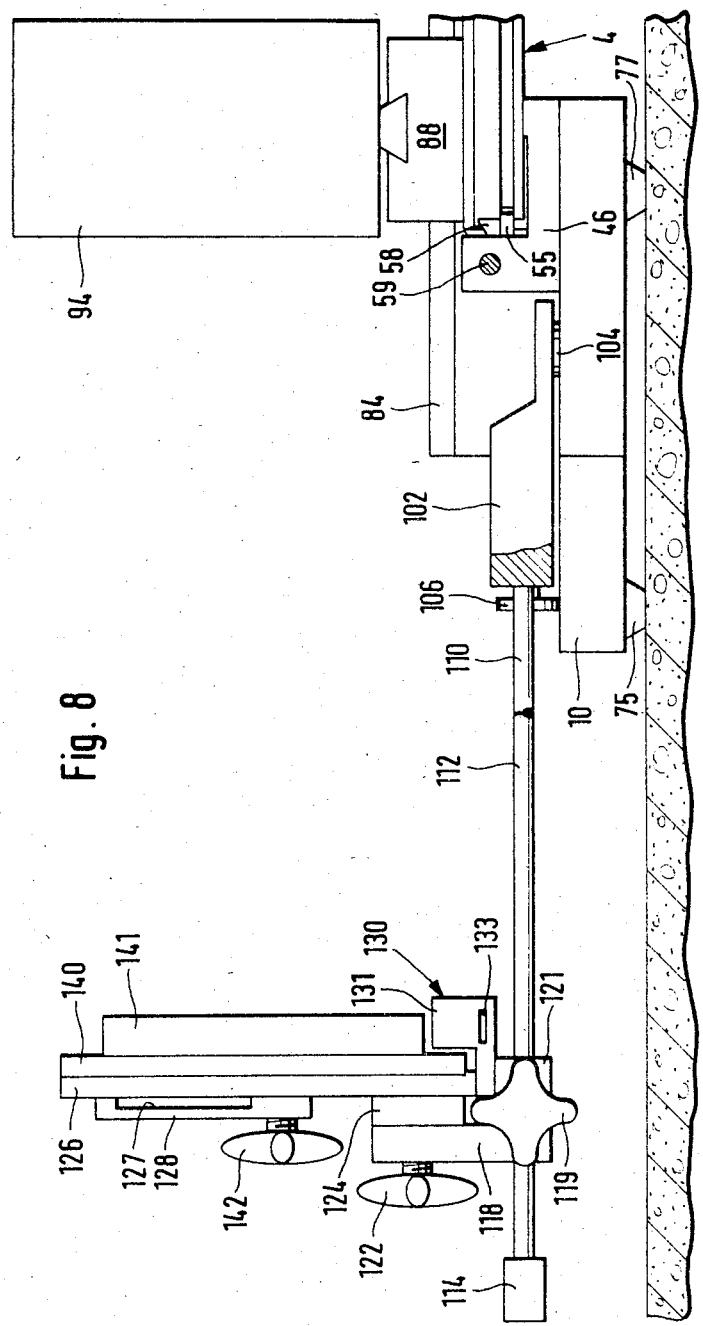

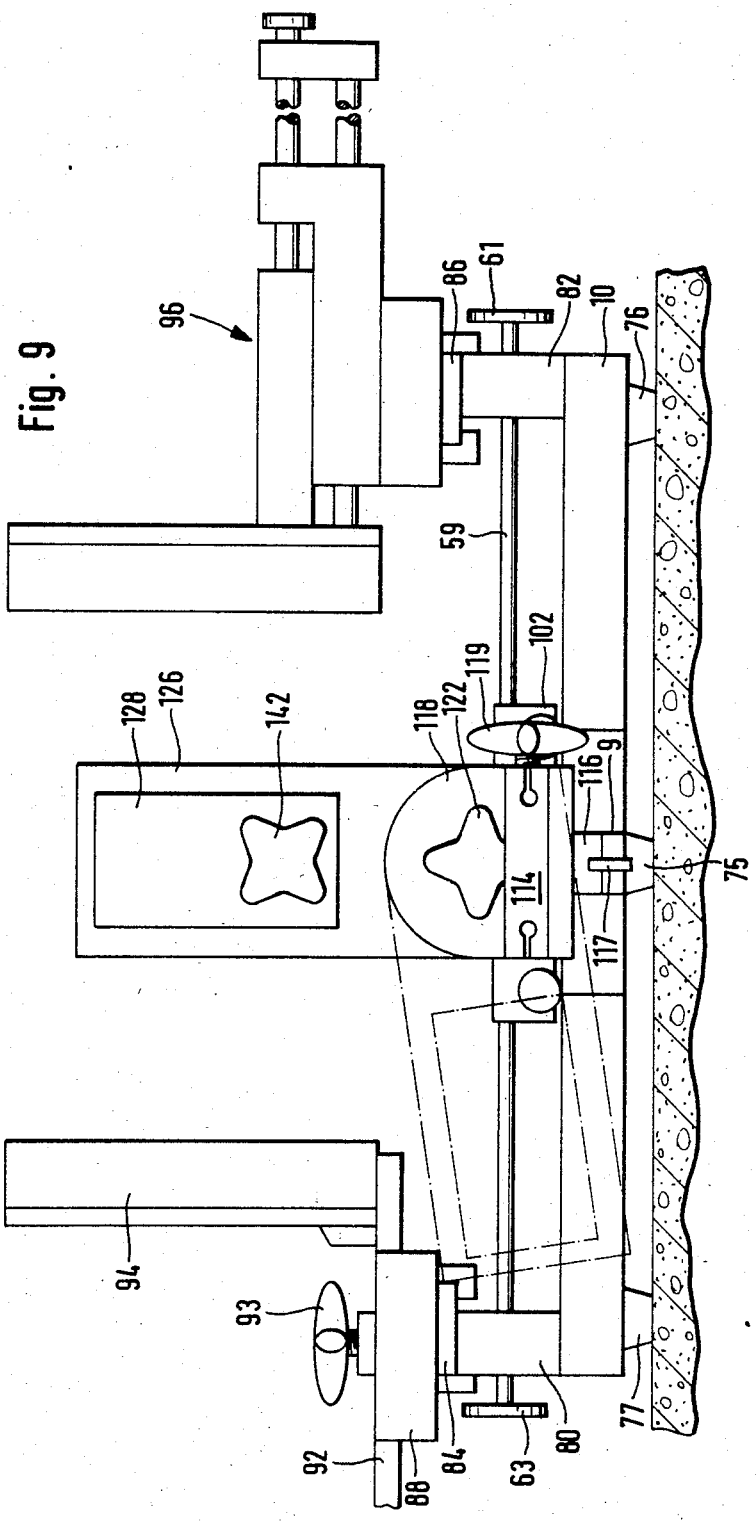

LEG-SUPPORT FOR MAKING RESTRAINED-OBJECT X-RAY PHOTOGRAPHS OF THE KNEE JOINT

BACKGROUND OF THE INVENTION—FIELD OF THE INVENTION

The invention relates to a supporting means for making restrained-object X-ray photographs (hereinafter: restrained X-ray photographs) of the knee joint.

BACKGROUND OF THE INVENTION—DESCRIPTION OF THE PRIOR ART

The nature and seriousness of injuries or damage to capsule ligaments of various joints can be directly discovered by an experienced traumatologist as a result of a thorough clinical examination. Evidence or a documentary record of the clinically established diagnosis, in addition to other methods, is represented by the restrained X-ray photograph of the joint in question and of the contralateral undamaged joint (see bibliography 2, 7, 8, 15). With certain joints, the technique as regards restrained X-ray photograph has progressed to such an extent that the instability of the joint which can be read off from the X-ray image can be determined quantitatively. The quantitative evaluation of the restrained X-ray photograph at the present time, in connection with certain joints, even forms the basis of reaching a decision as regards the therapy to be adoped (see bibliography 5). In addition, it serves for the control of the effect of therapy with check-up procedures (see bibliography 2, 15).

Because of the complexity of the capsule ligament structures, this standard has still not been reached by the restrained photograph of the knee joint, the consequence of which is that, as previously, the necessity and value of the restrained photographs of the knee joint are negated (see bibliography 1).

With the numerous methods as recommended in the literature for making restrained X-ray photographs of the knee joint, it is possible to differentiate between two fundamentally different supporting positions or stress effects.

1. The testing of the opening of the joint gap due to valgus stress medially and varus stress laterally in the path of ap-radiation;
2. The testing of the displacement of the head of the tibia with respect to the femur condyle by a "drawer movement" towards the front or towards the rear in the lateral path of rays (see bibliography 2, 15).

The response of the knee joint to be examined to the stress being exerted is dependent on several factors. They were established by experimentation and, in detail, read as follows (the numbers in brackets are references to the bibliography):

(a) extent of the capsule ligament lesion (2, 8)
(b) flexion position of the knee joint (4, 12, 16)
(c) rotational position of the tibia with respect to the femur (14)
(d) strength of the stress-exerting force (11)
(e) strength of the axial load (6, 10)
(f) extent of the strain on the muscle of the patient.

In order to be able to reach a conclusion from the restrained X-ray photograph as regards the extent of the capsule ligament lesion, it is necessary to keep the factors mentioned under (b) to (d) as constant and as defined as possible and to exclude, as far as possible, the factors which are mentioned under (e) and (f).

The strictly manually restrained X-ray photograph of the knee joint is no longer equal to the developed standards of modern knee joint diagnostics. Both the support of the proband leg (knee flexion and lower leg rotation) and the effort necessary for the examiner are subject to considerable individual variations, so that different dimensions of hingeability and "drawer" instability are reflected on the X-ray film (see bibliography 2). The manually restrained photograph loses its quantitative and in certain circumstances also its qualitative informativeness as regards examination conditions which are standardised and can be reproduced at any time.

Furthermore, the strictly manual photograph technique has the additional disadvantage of the effects of the radiation on the examiner, especially when the hand of the examiner exerting a rocking or pulling action on the knee joint is situated directly in the beam path (see bibliography 2, 15). In this case, even a lead glove does not offer any adequate protection.

Various appliances for making restrained X-ray photographs of the knee joint are on the market. However, in each case, they have certain serious disadvantages. The SCHEUBA arrangement (see bibliography 13), for example, does not compel any stable or defined position of the proband leg as regards flexion position of the knee joint and position of rotation of the lower leg in relation to the femur. During the examination, the patient is able to move into other positions.

As regards the examination chair of STANCOVIC (see bibliography 15) and, as with the GÄDE apparatus (see bibliography 2), the stable and defined flexure and rotational position for the "drawer" stress is assured. The disadvantage of both apparatus consists, however, in the fact that the proof of the lateral hingeability is not possible therewith and the "drawer" stress can only be conducted with a flexion of 90°, as a result of which "drawer" instabilities, which are only made noticeable in relatively small degrees of flexion, remain undiscovered.

SUMMARY OF THE PRESENT INVENTION

The novel X-ray apparatus is to have the following properties:

1. Both the lateral hingeability (medially and laterally) and the "drawer" instability (forwardly and rearwardly) are to be capable of detection.
2. The leg to be examined is to be adjustable in all arbitrary degrees of flexion between extension and 90° flexure in the "drawer" test.
3. The lower limb is to be adjustable in any desired positions of rotation between 30° inward rotation and 30° outward rotation.
4. The exertion of force when carrying out the stressing is to be defined.
5. The patient is to be able to adopt a recumbent position with muscles relaxed in the apparatus at the time of examination.
6. The apparatus is to be easily operated.

To this end, the novel supporting means is preferably split up into four main components:

1. a thigh section with two clamping jaws movable centrally relative to one another,
2. a stable ring which is fixed thereon and which has an angle indicating scale. The ring embraces the circular X-ray zone for the knee joint. The X-ray cassette is located beneath the said ring.

3. A lower leg section which can be swivelled towards both sides relatively to the thigh section and which can be stopped at a defined angular position. This section, with its parallel rails on both sides, is a carrier of so-called supports. A static support serves to support the knee with respect to the levering or displacing dynamic support. It is by means thereof that the stress needed at the time is exerted with a defined force on the proband knee.

4. A foot-supporting component with a lower leg rotation scale. The foot-supporting component or part is either capable of being rigidly fixed in the path of the longitudinal axis of the lower limb or deviates towards one side about a proximally disposed pivot point, according to the direction of the supporting thrust.

5. A facultatively usable femur condyle clamp for the range of application of the rearward "drawer" and hingeability in a deflecting position of 20°. This additional part is therefore not used for the functional regions of hingeability in the extended position and front "drawer".

Using this apparatus, it is possible, during an X-ray examination procedure, with constant adjustment of the X-ray apparatus as regards film-focusing distance and angle of incidence of the radiation, to test both the lateral hingeability and the "drawer" displaceability with the right and left leg in adjustable positions of rotation. The leg is so clamped in the apparatus that the interarticular space of the knee lies in the centre of the circular X-ray field. A marking of the skin over the interarticular space with a felt pen facilitates the adjustment.

The example of the isolated front cruciate lesion is intended to show, by way of example, the great influence which is exerted by the flexion and rotational position of the knee joint on the instability behaviour with the provision of restrained X-ray photographs. The utilisation of the "drawer" stress photographs with a flexion smaller than 90° is obvious.

Many experiments carried out on fresh cadaver knee joints have confirmed the phenomena of the instability behaviour of the knee joint under the effect of stress, these phenomena being known from clinical tests. As an example of the "drawer" instability of the isolated front cross-ligament lesion, it is possible to indicate, by way of example, the importance in respect of all forms of instability of exactly defined adjustment or setting of degrees of flexion or rotation of the proband knee joint. During the evaluation of the restrained X-ray photographs, it is possible to make use of the measurement methods of JACOBSEN (see bibliography 7), with which, in the lateral path of rays, both the medial and the lateral "drawer" instability (VSM and VSL) are established. The "drawer" instability values ($\Delta S$) are determined from the difference ($FT_{intact}$ minus $FT_{damaged}$). As a consequence, two values are obtained for each X-ray image, which values not only permit a conclusion on the "drawer" instability, but also an indication regarding the rotatory response to the "drawer" stress (VSM greater than VSL=outward rotation, VSM smaller than VSL=inward rotation). The "drawer" values determined on eight cadaver knee joints and with the isolated front cross-ligament lesion at 30° and 90° flexion show scarcely any forward shift at 90°, but on the contrary a distinct shift at 30°. This circumstance is taken into account in the LACHMANN test of the clinical investigation (see bibliography 4, 12, 16). Furthermore, the "drawer" values at 30° flexion show a greater forward movement of the lateral tibia head zone, i.e. a "drawer" with internal rotation. This phenomenon is also known from the pivot shift test (see bibliography 3, 9) and is not represented with the restrained "drawer" photograph in 90° flexion.

The essential features of the invention are defined in the accompanying claims. In so far as the claims do not contain essential features of the invention, these features can be derived from the accompanying drawing and also from the following description of the apparatus according to the invention.

BRIEF DESCRIPTION OF THE DRAWING

In the drawing:

FIG. 3 is a plan view of the thigh part;

FIG. 4 is an elevation of the upper part of the femur condyl clamp from the direction A in FIG. 3;

FIG. 8 is a side elevation of the lower leg part in the direction B from FIG. 7;

FIG. 9 is a view of the lower leg part from the rear in the direction C (FIG. 7).

DETAILED DESCRIPTION OF THE PREFERRED EMBODIMENT

Figure 1:
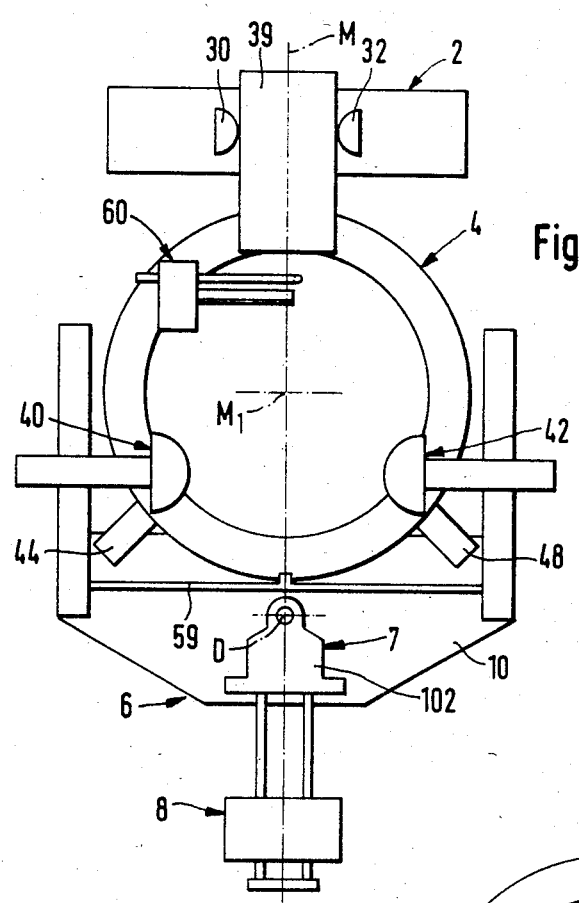
FIG. 1 is a diagrammatic plan view of the holding means in the functional position for the hingeability test.
Figure 2:
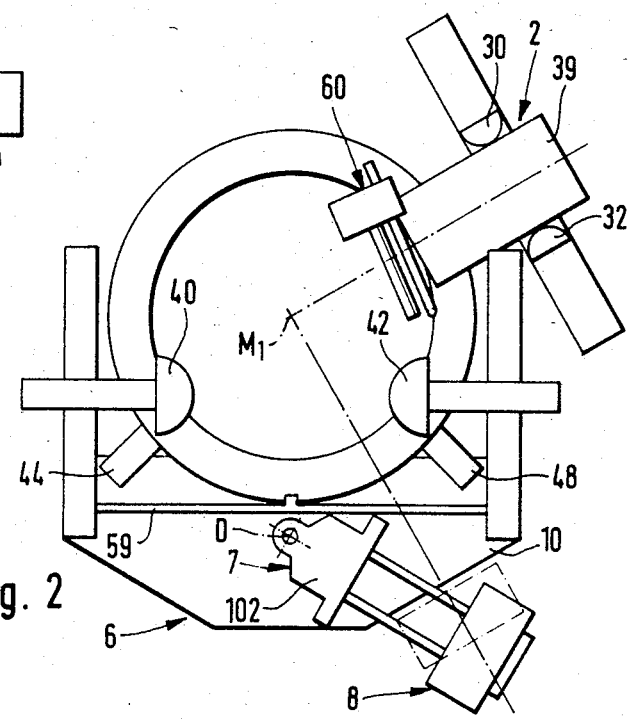
FIG. 2 is a view of the holding means which is similar to FIG. 1 and in which the thigh part and the lower leg part are adjusted in the direction of a 60° flexion, and in fact in the functional position for the "drawer" test.

The holding means or appliance mounted on a base plate 10 symmetrically of the centre line M consists, in the form in which it is illustrated in FIGS. 1 and 2, and seen from right to left, of a thigh part 2 with clamping elements 30, 32 arranged symmetrically of the centre line M, a ring 4 which is connected to the thigh part 2 and on which the base plate 10 is fixed for rotatable movement about its centre point $M_1$, and of a lower leg part 6, consisting of two rails 84, 86 which are fixed in parallel relationship on the base plate 10 on both sides of the ring 4 and which are provided for static or dynamic supports (power supply means) 40, 42 and an adjusting means 58, 59 for fixing the angle for the setting of the base plate 10 in relation to the ring 4. Fixed on the base plate 10 of the lower leg part 6 is a longitudinally movable foot part 7, which consists of a block 102 which can be swivelled about the pivot point D, a pair of rods 110, 112 and a foot-holding portion or part 8. The lower leg part or a member 6 is capable of being swivelled relatively to the ring 4 about the centre point $M^1$ of the ring towards both sides relative to the centre line M and in each case by 90°. The foot member 7 with the foot-holding part 8 can be swung out on both sides of the centre line M about the pivot point d, in each case through at least 45°.

Figure 5:
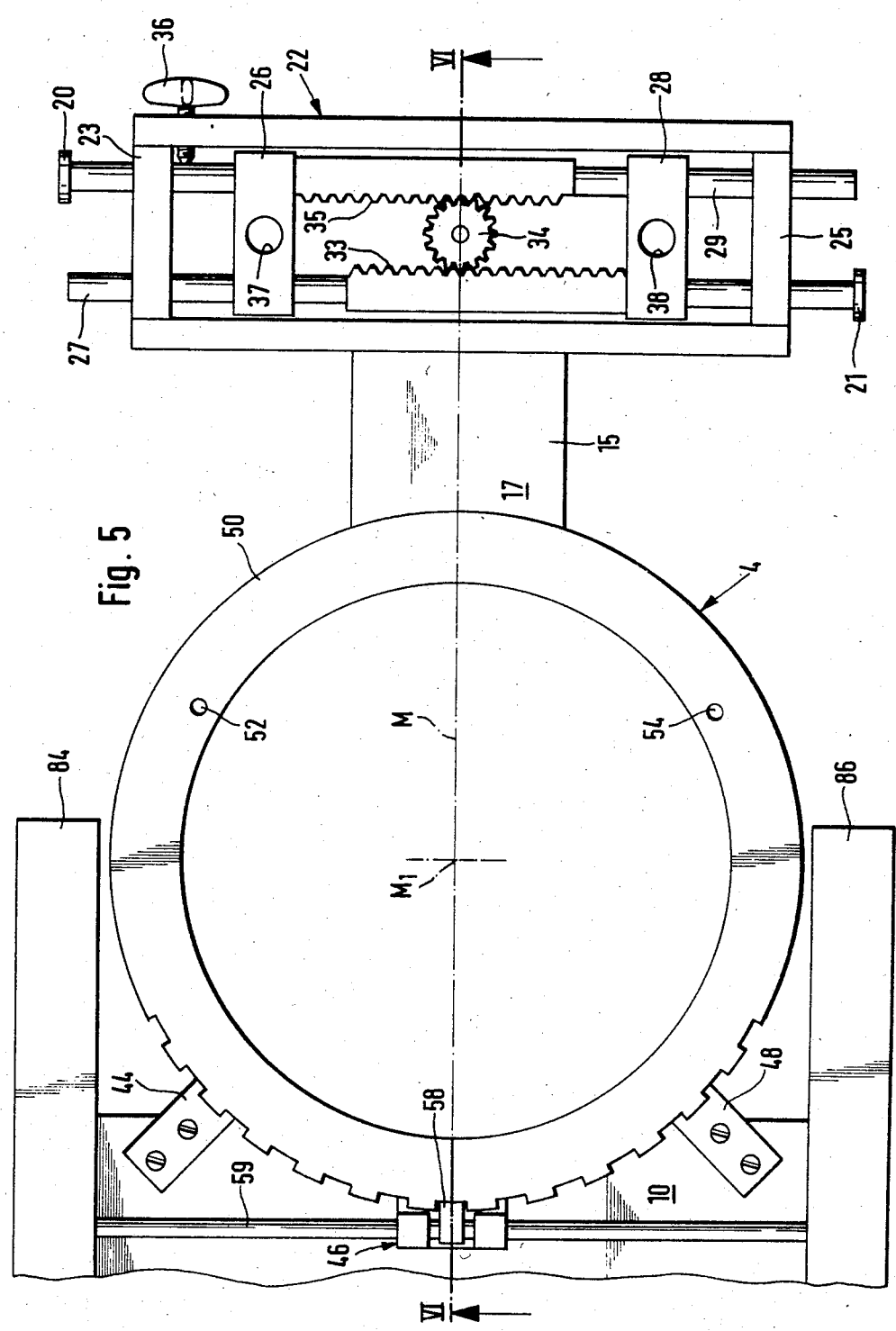
FIG. 5 is a plan view of the opened thigh part with a fitted ring.
Figure 6:
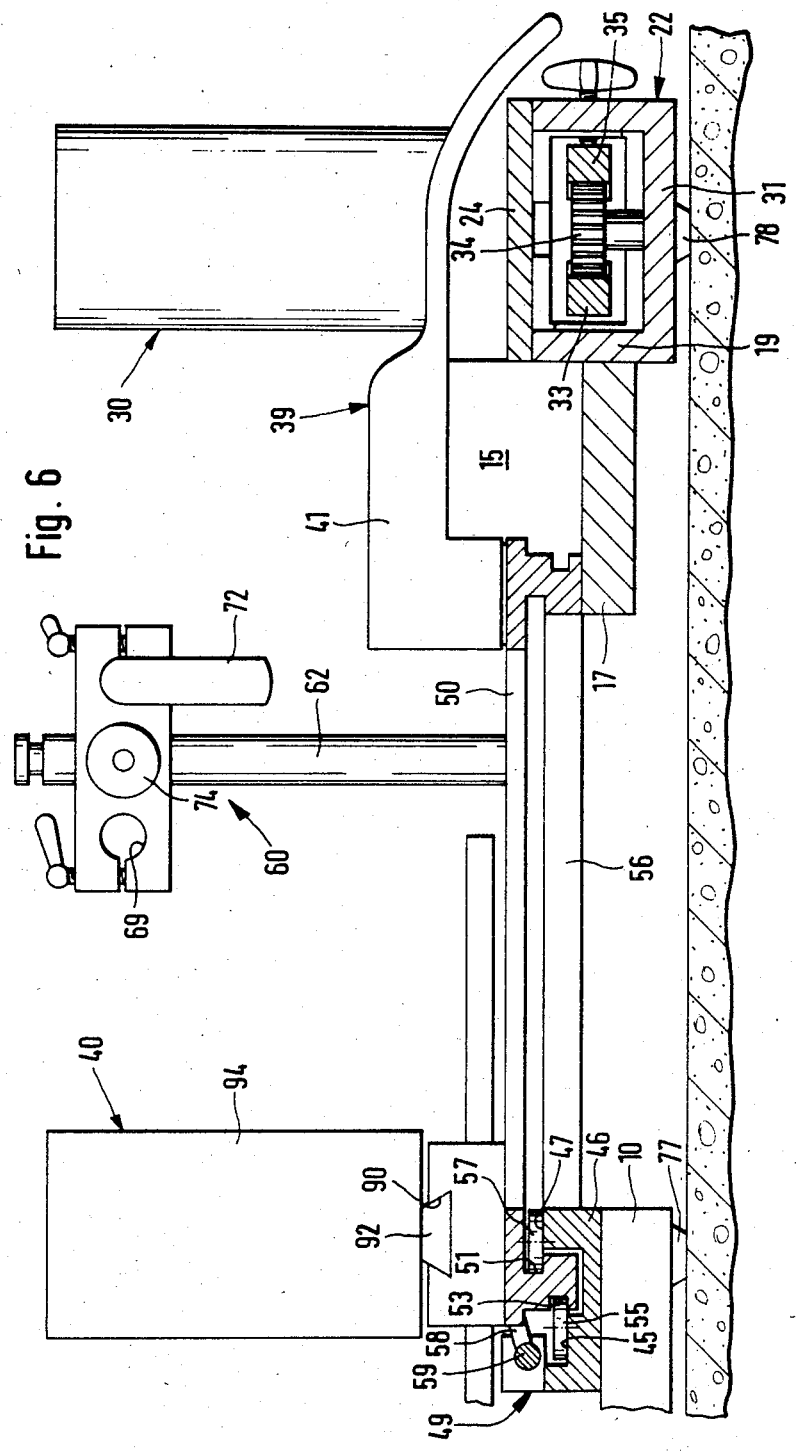
FIG. 6 is a side view of the section along the line VI—VI of FIG. 5, with additional parts of the holding means.

According to FIGS. 3, 5 and 6, the thigh part 2 comprises a rectangular box or casing 22 extending, spaced from the ring 4, transversely of the centre line M and symmetrically of this latter, the upper open end of the said casing or box being substantially closed or sealed off by means of a screwthreaded cover 24. Two supports 26, 28 which are coupled to one another are mounted for displacement transversely of the centre line M inside the casing 22, the said supports being on both sides of the centre line M and each at an equal spacing from the latter. The support 26 is connected fast to a rod 27, which is extended outwardly through the facing side cheeks 23, 25 of the casing 22 and is provided on its outer end with a handle 21. The support 28 which is opposite the support 26 in relation to the centre line M is arranged to be displaceable on the rod 27. A central section of the rod 27 between the supports 26 and 28 is provided with a rack 33.

A rod 29 extends parallel to the rod 27 and spaced from the latter through the casing 22 and the side cheeks 23, 25 thereof, carries at one outer end thereof a handle 20, is connected fast to the support 28 and comprises a rack 35 in a central portion between the supports 26 and 28. The support 26 displaceably encloses the rod 29. The racks 33 and 35 are so designed and are so spaced that a pinion 34 rotatably mounted in the base 31 of the casing 22 on the centre line M meshes with both racks 33, 35. A clamping screw 36 extending through an outside wall of the casing 22 is able to bear against the rod 22 and secure the latter.

The support 26 and the support 28 are formed with an upwardly open central bore 37 and 38, respectively, into which can be fitted retainer pins 12, 14 of the clamping elements 30, 32. The cover 24 is formed on each of the two sides of the centre line M with a longitudinal slot 16 or 18, which permits the access to the bores 37, 38 along the path of displacement of the supports 26, 28. Each of the two clamping elements 30, 32 has a shape and construction such as that which is shown and described in connection with FIGS. 2–4 of German Offenlegungsschrift No. 31 31 472.

As may be easily understood, both clamping elements 30, 32, by pulling out or pushing in the rod 27 on the handle 21 and/or the rod 29 on the handle 20, and because of the coupling through the pinion 34, can always be displaced symmetrically away from the centre line M or towards this latter.

Screwed on to the central portion of the cover 24 is a shell 39 of a synthetic plastic which is not harmful to the skin and of which the trough-shaped part 41 extends from the casing 22 to beyond the periphery of the ring 4 and can be supported on this latter.

Fitted on to that side wall 19 of the casing 22 which faces the ring 4 and in the central section of the casing 22 is a holding plate 17, which engages with a supporting action beneath the section of the ring 4 close to the casing and is fixed to the latter. Left above the holding plate 17 is a space 15, into which the end of one of the rails 84, 86 is able to extend when the thigh part 2 is twisted relatively to the lower leg part 6 from the centre line M. The brass ring 4 is held so as to be unable to tilt on the peripheral portion opposite the thigh part 2 in three blocks 44, 46, 48 by means of altogether eight ball bearings, so that it is rotatable together with the thigh portion 2 about is centre point $M_1$. According to FIG. 6, the brass ring 4, which is cast in one piece, comprises an upper rim 50, in the external circumference of which, adjacent to blocks 44, 46, 48, are provided several incisions of equal width and equal spacing in the manner of a graduated scale. Drilled in the peripheral section of the rim 50 between the centre point $M_1$ of the ring and the trough-shaped member 41 are two oppositely disposed holes 52, 54, into which can be fitted the stem of a femur condyle clamp 62 represented as a whole by 60.

The annular member 56 adjoining the rim 50 on the underside has a first annular groove 51 close beneath the rim 50, which groove is cut in the member 56. A second annular groove 53 is cut in the external face of the member 56 beneath the first annular groove 51.

The blocks 44, 46, 48 are screwed or bolted to the base plate 10. As shown in FIG. 6, using the midle block 46 as an example, each of the blocks has an outer bearing surface 45, on which is fixed the inner race of an outer ball bearing 55. The outer race of the said ball bearing runs on the bottom of the second annular groove 53. Fixed on the inner bearing surface 47 of the middle block 46 is the inner race of an inner ball bearing 57, the outer race of which runs on the bottom of the first annular groove 51. Each of the lateral blocks 44, 48 is equipped with an inner ball bearing and an outer ball bearing. The middle block 46 carries two pairs of such ball bearings, which are spaced relatively to the circumference of the ring 4. In this way, the ring 4 is supported for rotational movement by eight ball bearings. The middle block 46 has a through bore on an upper section 49, through which is passed a shaft 59. In a cut-out of the upper section 49, the shaft 59 carries a projection 58 which cannot be turned and is at such a distance from the adjacent periphery of the rim 50 that, by rotation of the shaft 59, the projection 158 is able to drop, substantially without play, into one of the said cutouts in the periphery of the rim 50. In this position of the projection 58, the ring 4 is blocked against rotational movement. The projection 58 and the cut-out of the upper section 49 of the middle block 46 are arranged between the two pairs of ball bearings with which the middle block 46 is equipped. According to FIG. 9, the shaft 59 extends parallel to and transversely over the base plate 10 and outwardly through lateral blocks 80, 82 and carries a handle 61 or 63 at each of its outer ends.

The femur condyle clamp 60, which can be seen in FIGS. 3, 4 and 6, consists of a round post or rod 62 formed with a longitudinal groove 64 and a support block 66, which is displaceable along the post 62 after loosening a clamping screw 65 which engages in the longitudinal groove 64. At the upper end, the post is formed with an encircling recess 67, which allows a free rotation of the support block 66 about the axis of the post 62 when the clamping screw 65 is not completely screwed out of the support block 66. The support block has, on both sides of its central bore which embraces the post 62, two through bores 68, 69 which extend transversely of the central bore and which respectively serve for receiving a hooked rod 70, which can consist of a material transmitting X-rays. The hooked rod 70 has a bent-over hook 72 at one end. In addition, the support block 66 is formed with a blind hole which is disposed parallel to the through bores 68 and into which is fitted a fixed clamp rod 74 of a material transmissive for X-rays, which rod serves for pressing down a thigh resting on the shell or tray 39 and for engaging behind the inner femur condyle. It is possible by means of the hooked rod 70 to hold the thigh in an axial middle position in the centre line M.

Fixed on each of the elongated blocks 80, 82 is a rail 84, 86, the said rail projecting freely at its end facing the thigh part or section 2 approximately as far as the centre point of the ring 4 (FIG. 5). Displaceable longitudinally on the rail 84 is a slide member 88, in which is formed, from above, a groove 90 which is dove-tailed in crosssection, the said groove extending transversely of the rail 84 and therefore transversely of the centre line M. Fitted for longitudinal displacement in the groove 90 is a bar or fillet 92, at the end of which is formed a bore for receiving a pressure-applying member 94. This latter member 94 corresponds in its construction and shape to the clamping member 30 or 32. A clamping screw 93 permits the bar or fillet 92 to be so stopped and secured in the groove 90 that the pressure-applying member 94 maintains a required spacing with respect to the centre line M.

Fixed to the block 82 secured on the opposite longitudinal edge of the base plate 10 is the rail 86, which extends parallel to the rail 84 and is of the same length as this latter. A pressure-applying member corresponding to the pressuring chamber 94 can be fitted by means of cursors on the rail 86 (not shown) but alternatively it is also possible, as illustrated, for a pressure-measuring device 96 according to FIGS. 1 and 9 of German Offenlegungsschrift No. 31 31 472 to be mounted on the rail 86, which device is displaceable along the rail into a required position. The pressuring part 94 and the pressure-measuring device 96 serve the purpose of applying a defined pressure which can be read off on the pressure-measuring device 96 to the lower limb just beneath the knee.

Figure 7:
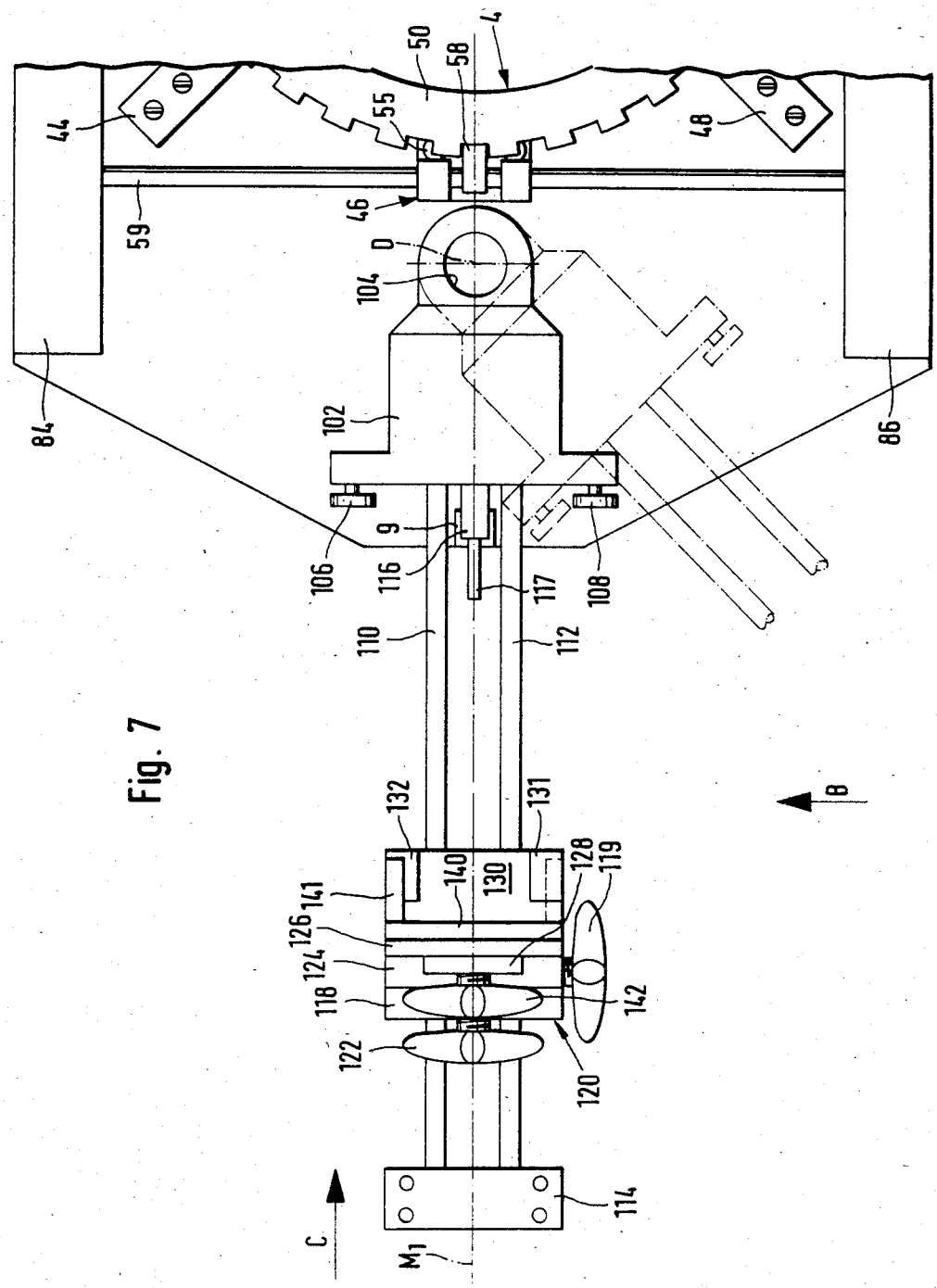
FIG. 7 is a plan view of the lower leg part of the holding means.

The lower limb section 6 with the foot section 7, as illustrated in FIGS. 7 to 9, consists of a pivot block 102 which is mounted on the base plate 10 and of which the end facing the ring 4 is anchored by means of a coupling 104 in the base plate 10. Fixed on the end face remote from the ring 4 and on both sides of the centre line M are two rollers 106, 108, so that the pivot block 102 is rotatable towards both sides of the centre line M about that pivot point D of the coupling or joint 104 which is on the centre line M and is supported by means of the coupling 104 and the rollers 106, 108 on the base plate 10. A round rod 110, 112 is in each case clamped with a tight fit in two bores (not shown) of the pivot block 102, the said bores extending symmetrically with respect to the centre line M and parallel to the latter. At the free ends projecting beyond the base plate 10, the rods 110, 112 are so held in spaced relation by a clamping block 114 that they extend parallel to one another. Rotatably mounted in the pivot block 102 and in the surface facing away from the ring 4 is a lever 116 with a handle 117, which can be so positioned in a recess 9 of the base plate 10 as to fix the mean position of the pivot block 102 facing the centre line M. Indicated in FIG. 7 in broken lines is a position of the pivot block 102 in which it is swivelled relatively to the centre line M.

The foot-supporting member 8 comprises an angle member 120, of which the lower leg 121 is formed with two through bores, through which the rods 110, 112 extend. A clamping screw 119, which passes laterally through the lower leg 121, makes it possible for the foot-supporting member, which otherwise is freely movable on the rods 110, 112, to be fixed in any desired position. The vertical leg 118 of the angle member 120 has an upwardly pointing, semi-circular bounding surface and also a bore for a screw 122, which extends through the upright leg 118 into a washer 124. The diameter of the washer or disc 124 is equal to the width of the upright leg 118 and terminates with this latter. Engraved on its periphery is a graduated scale, so that it is possible, by slackening off the screw 122, for the washer or disc 124 to be turned towards the left or right relatively to the angle member 120 and respectively of its upright leg 118 in the embodiment which is shown in FIG. 9. The disc 124 is immovably fixed to the bottom end of a plate 126 extending parallel to the leg 118, it being possible for this plate to be of the same width as the leg 118. The upper part of the plate 126 is provided with an attachment 128 on the external surface which is facing the leg 118, which attachment has a slot 127 towards the plate 126, through which it is possible to pull a strap (not shown). Fixed on the bottom end of the plate 126 is a heel support 130 which faces the pivot block 102 and on which it is possible for the heel of a patient to be placed in position between two lateral reinforcements 131, 132.

A foot plate 140, by means of a screw 142 which is rotatable in the foot plate 140 and which extends through a threaded hole in the member 128 and the plate 126, is held against that surface of the plate 126 which is facing the pivot block 126. The foot plate 140 has a longitudinal strip 141 on one side. The foot plate 140, with its longitudinal strip 141 and also the heel support 130, consist of a synthetic plastics material which is harmless to the skin. By slacking off the screw 142, the foot plate 140 can be turned through 180° about an axis parallel to the rods 110, 112, so that then the longitudinal strip 141 assume the position indicated in broken lines in FIG. 7. The foot of the patient, whose heel is resting on the heel support 130, can thus be laid against the foot plate 140 and the instep of the foot against the longitudinal strip 141. The heel support additionally comprises a slot 133, through which it is possible to pass another strap for securing the foot on the heel support. The previously mentioned strap which is pulled through the slot 127 makes possible the securing of the foot on the foot plate 140.

By loosening the screw 122, it is possible for the plate 126 with the heel support 130 and foot plate 114, in conformity with what is shown in FIG. 9, to be rotated towards the left or right about an axis parallel to the rods 110, 112, until approximately in the lateral position on both sides as shown in broken lines in FIG. 9. As a consequence, the foot which is held on the foot plate 140 and the heel support 130 can have imposed thereon a twisting movement, the angle of which is determined and can be read off on the graduated scale on the disc 124.

The fact that the pivot point D of the pivot block 102 is situated outside the centre point $M_1$ of the ring 4 has no harmful effect during the treatment of the patient, since by slackening off the clamping screw 119, the foot-supporting member 8 is adaptable without any difficulty to the radius related in each case to the point $M_1$ by longitudinal displacement along the rods 110, 112.

It is possible for the holding means or apparatus as described to be set up on any table on which the base plate 10 rests with the feet 75, 76, 77 and the thigh section 2 rests with corresponding feet (only the foot 78 is to be seen in FIG. 6).

It is within the scope of the invention for the foot-supporting member 8 to be so constructed that the plate 126 with its heel support 130 and foot plate 140 is capable of being turned about a vertical axis which is perpendicular to the plane formed by the rods 110, 112. For this purpose, the angle member 120 can be mounted by means of a linkage or joint on a slide which is not shown and which is displaceable longitudinally on the rods 110, 112. One position of the foot-supporting part in a position rotated about the vertical axis is shown in broken lines in FIG. 2. It is possible thereby for the foot plate and the heel support to be adapted to a position of the foot at the time of adjusting the holding or supporting means according to FIG. 2.

The thigh section or member 2 can be rotated with the ring beyond the position which is shown in FIG. 2 and still further towards the base plate 10 with the ring, and in fact as far as a 90° position relatively to the centre line M (FIG. 1). The rail 86, or respectively the rail 84, with rotation of the thigh member 2 to the other side of the centre line M, in such a case find a free passage in the space 15 beneath the trough 41 of the shell 39, this not being visible with the arrangement of the holding means as shown according to FIGS. 5 and 6.

It also comes within the scope of the invention for the adjustment means to be so developed that the shaft 59 is constructed as a spindle which can be locked and which engages without any clearance in an external toothing on the periphery of the ring 4. What is hereby provided is the possibility of an infinitely adjustable rotation of the thigh member 2 relatively to the lower leg member 6.

LITERATURE (1) Franke J: (1981) Klassifikation der chronischen Kniebandinstabilitäten des Kniegelenkes. (Classification of the chronic knee ligament instabilities of the knee joint.) Teil I: Anatomie und Diagnostik. Beitr. Orthop. u. Traumatol. 28:125.

(2) Gade EA; (1980), Ein Messgerät zur objektiven Festellung der Instabilität des Kniegelenkes. (A measuring instrument for objectively determining the instability of the knee joint.) Orthop. Praxis 16:850.

(3) Galway HR, MacIntosh DL (1980) The Lateral Pivot Shift: a Symptom and Sign of Anterior Cruciate Ligament Insufficiency. Clin. Orthop. 147:45.

(4) Hafner H, Wirth CJ (1981) Experimentelle Untersuchungen zur Erklärung des LACHMANN-Testes. (Experimental investigations for explaining the LACHMANN test.) In: Jager, Hackenbroch, Refior: Kapselbandverletzungen des Kniegelenkes, Experimentelle Grundlagen der Diagnostik und Therapie Thieme Stuttgart S. 123-128.

(5) Hagen P, Rehm K, Hausel M (1981) Abgrenzung der operativen und konservativen Behandlung frischer Bandverletzungen am oberen Sprunggelenk. (Limitation of the operative and conservative treatment of fresh damage to ligaments on the upper ankle joint). Orthop. Praxis 17:324.

(6) Hsieh HH, Walter P (1976) Stabilizing Mechanisms of the Loaded and Unloaded Knee. J. Bone Jt. Surg. 58A:87.

(7) Jacobsen K (1977) Radiologic Technique for Measuring Instability in the Knee Joint. Acta Radiolog. Dign. 18:113.

(8) Jager M, Wirth CJ (1980) Die Problematik veralteter, kombinierter Komplexinstabilitaten des Kniegelenkes. (The Problems of old, combined complex instabilities of the knee joint) Unfallheilkunde 82:84.

(9) Losee RE, Johnson TR, Southwick WO (1978) Anterior Subluxation of the Lateral Tibial Plateau. A Diagnostic Test and Operative Repair. J. Bone Jt. Surg. 60A:1015.

(10) Markolf KL, Bargar WL, Shoemaker SC, Amstutz HC (1981) The Role of the Joint Load in Knee Stability. J. Bone Jt. Surg. 63A:570.

(11) Nayes FR, Grood ES, Butler DL, Malek M (1980) Clinical Laxity Tests and Functional Stability of the Knee: Biochemical Concepts. Clin. Orthop. 146:84.

(12) Rodriguez M, Suezawa Y, Jacob HAC (1981) Experimentelle Untersuchungen zur Diagnostik des Kniebandapparates. (Experimental investigations concerning the diagnostics of the ligament apparatus.) In: Jager, Hackenbroch, Refior: Kapselbandverletzungen des Kniegelenkes. Experimentelle Grundlagen der Diagnostik and Therapie. Thieme Stuttgart S. 93-97.

(13) Scheuba (1981) Die gehaltene Aufnahme (The restrained photograph). Prospekt der Firma Telos Griesheim.

(14) Slocum DB, Larson RL (1968) Rotatory Instability of the Knee. J. Bone Jt. Surg. 50A:211.

(15) Stankovic P, Zurcher K, Stuhler Th, Heise A (1979) Zur rötgenologischen Diagnostik von Kapselbandverletzungen am Kniegelenk. (Concerning radiological diagnosis of damages to the ligaments of the knee joint.) Chirurg 50:658.

(16) Torg JS, Conrad W, Kalen V (1976) Clinical diagnosis of Anterior Cruciate Ligament Instability in the Athlete. Am. J. Sports Med. 4:84.

We claim:

1. Leg support means for receiving the knee joint and connecting parts of the thigh and lower leg of a patient for making restrained X-ray photographs of the knee joint, said leg support means comprising:
   a base member;
   a lower leg section mounted on said base member for receiving the lower leg of the patient;
   a thigh section having two clamping posts mounted thereon for movement toward and away from each other for receiving the thigh of the patient therebetween;
   a ring, the leg of the patient being adapted to lay across the ring with the knee joint located in alignment with the interior thereof when the lower leg and thigh of the patient are received in the lower leg section and thigh section, respectively, said ring being rotatably mounted on said base member and fastened to said thigh section for rotating said thigh section with respect to said lower leg section up to 90° on either side of a central position in which said lower leg section and thigh section are generally aligned; and
   a foot member mounted on said base member for pivotal movement with respect to said lower leg section.

2. The leg support means according to claim 1 wherein said lower leg section comprises two parallel rails containing supports for the lower leg of the patient, one of said parallel rails lying on either side of said ring; said lower leg section further including an adjustment means for said ring extending between said rails and containing means for retaining said ring in a desired rotary position with respect to said lower leg section.

3. The leg support means according to claim 2 wherein said ring has an external periphery containing a plurality of angularly displaced incisions and wherein said adjustment means comprises a locking projection engaging with said incisions for retaining ring in a desired rotary position.

4. The leg support means according to claim 2 wherein said ring has a center line extending parallel to said rails and containing the center of said ring and wherein a support means for the lower leg of the patient is mounted on each of said rails for movement parallel to said center line and toward and away from said center line.

5. The leg support means according to claim 4 wherein at least one of said supports comprises a pressure-measuring instrument.

6. The leg support means according to claim 1 wherein said foot member is mounted on said base member externally of said ring.

7. The leg support means according to claim 6 wherein said lower leg section has a center line containing the center of said ring and wherein said foot member is mounted on said base member along said center line.

8. The leg support means according to claim 1 wherein said foot member includes a foot supporting part mounted on said foot member for movement with respect to the remaining portions of said foot member.

9. The leg support means according to claim 8 wherein said foot member comprises a pivot block rotatably mounted on said base member; a pair of parallel rods extending from said pivot block; and said foot supporting part mounted on said rods for movement therealong.

10. The leg support means according to claim 9 wherein said foot supporting part comprises a foot plate and a heel support member.

11. The leg support means according to claim 10 wherein said foot plate is rotatably mounted on said foot supporting part for rotation through at least 240° relative to said foot supporting part.

12. The leg support means according to claim 11 wherein said ring is a planar ring and wherein said foot plate and heel support are rotatably mounted on said foot supporting part for rotation in either direction from a central position about an axis parallel to the plane of said ring.

13. The leg supporting means according to claim 10 wherein said ring is a planar ring and wherein said foot plate and heel support are rotatably mounted on said foot supporting part for rotation in either direction from a central position about an axis parallel to the plane of said ring.

14. The leg support means according to claim 1 wherein said ring has an external periphery containing a plurality of angularly displaced incisions for establishing the rotary position of said ring.

15. The leg support means according to claim 1 wherein said ring includes a plurality of annular grooves and wherein said base member includes bearing means engaging said grooves for mounting said ring on said base member in a rotatable and non-tiltable manner.

16. The leg support means according to claim 1 wherein said ring is mounted on said base plate by three angularly spaced blocks.

17. The leg support means according to claim 1 further including a femur condyle clamp mounted on said ring in proximity to said thigh section.

18. The leg support means according to claim 17 wherein said thigh section has a center line and wherein said femur condyle clamp comprises a hooked rod mounted on said ring for movement transversely of said center line of said thigh section.

19. The leg support means according to claim 18 wherein said femur condyle clamp comprises a clamping rod.

20. The leg support means according to claim 18 wherein said hooked rod is formed of a material transmissive for X-rays.

21. The leg support means according to claim 17 wherein said femur condyle clamp comprises a clamping rod.

22. The leg support means according to claim 21 wherein said clamping rod comprises a material transmissive for X-rays.

23. The leg support means according to claim 1 wherein said thigh section has a center line and wherein said clamping posts are arranged on either side of said center line.

24. The leg support means according to claim 23 wherein said thigh section includes means coupling said clamping posts for concentrically moving them toward and away from said center line.

* * * * *